United States Patent
Ireland

(10) Patent No.: US 9,579,087 B2
(45) Date of Patent: *Feb. 28, 2017

(54) FLEXIBLE BIOPSY NEEDLE

(75) Inventor: Dan C. Ireland, Martinsville, IN (US)

(73) Assignee: Promex Technologies, LLC, Franklin, IN (US)

(*) Notice: Subject to any disclaimer, the term of this patent is extended or adjusted under 35 U.S.C. 154(b) by 1153 days.

This patent is subject to a terminal disclaimer.

(21) Appl. No.: 13/296,906

(22) Filed: Nov. 15, 2011

(65) Prior Publication Data

US 2012/0065543 A1  Mar. 15, 2012

Related U.S. Application Data

(63) Continuation of application No. 12/788,444, filed on May 27, 2010, now Pat. No. 8,057,403.

(60) Provisional application No. 61/182,248, filed on May 29, 2009.

(51) Int. Cl.
*A61B 10/00* (2006.01)
*A61B 10/02* (2006.01)

(52) U.S. Cl.
CPC ...... *A61B 10/0275* (2013.01); *A61B 10/0233* (2013.01); *A61B 10/0266* (2013.01)

(58) Field of Classification Search
CPC . A61B 10/0275; A61B 10/02; A61B 10/0233; A61B 10/0266; A61M 25/0051; A61M 25/0052; A61M 25/0053; A61M 25/0054; A61M 2025/0063; A61M 25/0102; A61M 25/0138

USPC ........ 600/562, 564, 567; 606/167, 170, 171; 604/528

See application file for complete search history.

(56) References Cited

U.S. PATENT DOCUMENTS

| | | | |
|---|---|---|---|
| 4,246,902 A | 1/1981 | Martinez | |
| 5,106,364 A | 4/1992 | Hayafuji et al. | |
| 5,171,222 A * | 12/1992 | Euteneuer et al. | 604/103.1 |
| 5,320,110 A | 6/1994 | Wang | |
| 5,669,926 A * | 9/1997 | Aust et al. | 606/170 |
| 5,797,907 A | 8/1998 | Clement | |
| 5,851,212 A | 12/1998 | Zirps et al. | |
| 5,989,196 A | 11/1999 | Chu et al. | |
| 5,997,560 A | 12/1999 | Miller | |
| 6,027,514 A | 2/2000 | Stine et al. | |
| 6,251,120 B1 | 6/2001 | Dorn | |
| 6,296,624 B1 | 10/2001 | Gerber et al. | |
| 6,419,641 B1 | 7/2002 | Mark et al. | |
| 6,450,938 B1 * | 9/2002 | Miller | 600/7 |
| 7,699,792 B2 * | 4/2010 | Hofmann et al. | 600/585 |
| 8,057,403 B2 * | 11/2011 | Ireland | 600/567 |
| 2005/0209631 A1 * | 9/2005 | Galdonik et al. | 606/200 |

* cited by examiner

*Primary Examiner* — Max Hindenburg
(74) *Attorney, Agent, or Firm* — IpHorgan Ltd.

(57) ABSTRACT

A flexible biopsy needle assembly includes a flexible coring stylet that is slidably disposed within a flexible outer cannula. The stylet includes an elongated body, a tip, a sampling notch adjacent to the tip, and at least one ferrule along the length of the body. The cannula includes an elongated tubular body defining a lumen sized for sliding passage of the stylet, a cutting edge at the opening of the lumen, and an array of slits along the length of its body. The slits are sized to allow the diameter of the ferrule(s) to extend partially therein. The slits and ferrule(s) interact to limit or control the flexibility of the cannula at the location of the slits.

15 Claims, 3 Drawing Sheets

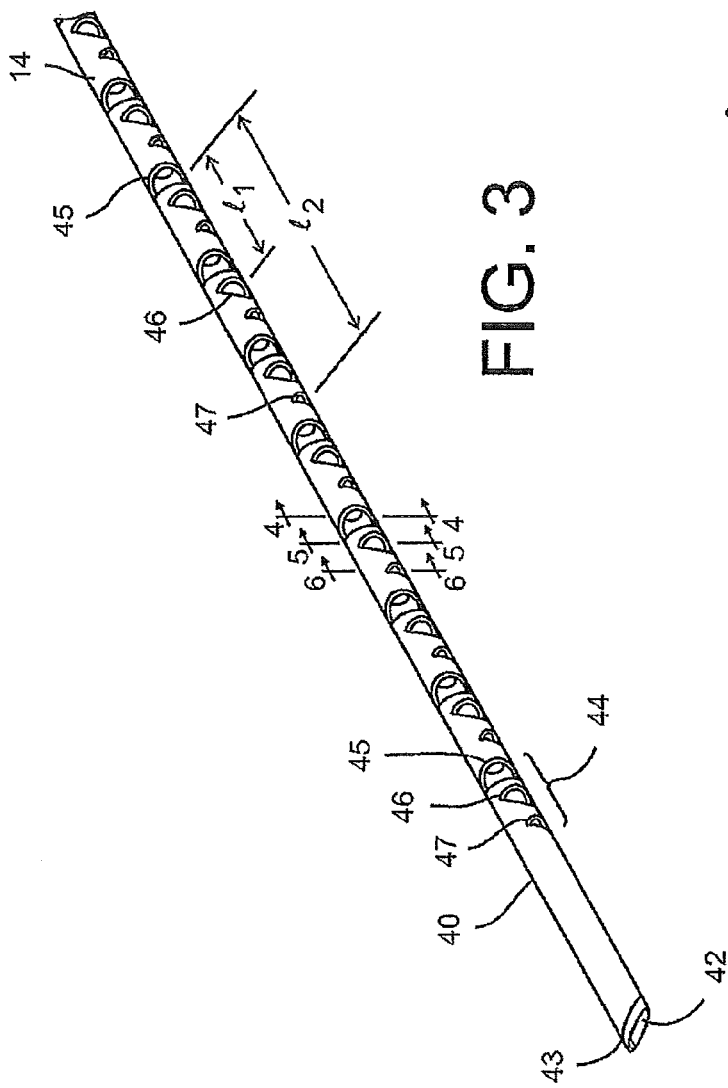
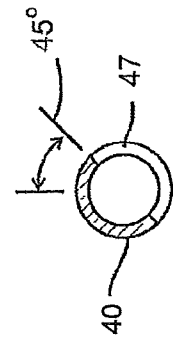
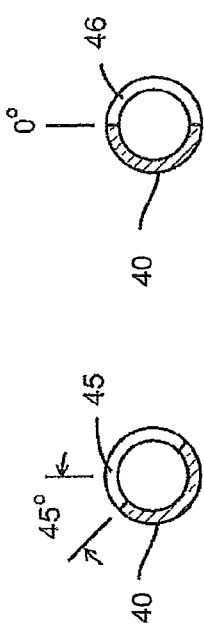

FLEXIBLE BIOPSY NEEDLE

REFERENCE TO RELATED APPLICATION

This application claims priority to and is a continuation of U.S. application Ser. No. 12/788,444, filed May 27, 2010, now U.S. Pat. No. 8,057,403, which claims the benefit of U.S. provisional application No. 61/182,248, filed May 29, 2009, the disclosure of each is incorporated herein by reference.

BACKGROUND

The present disclosure relates generally to biopsy systems and specifically to devices for obtaining biopsy samples through veins and arteries.

In the practice of diagnostic medicine, it is often necessary or desirable to perform a biopsy, or to sample selected tissue from a living patient for medical evaluation. Cytological and histological studies of the biopsy sample can then be performed as an aid to diagnosing and treating various forms of cancer, as well as other diseases in which a localized area of affected tissue can be identified.

Special considerations apply if the biopsy is to be performed on an internal organ deep within the body, such as the liver. Previously, obtaining a tissue sample from an internal organ, such as the liver, was carried out percutaneously by entering the skin in the vicinity of the organ and thereafter extracting a core of liver material through the biopsy needle. This method, although effective in obtaining an adequate amount of tissue from the liver, has a risk of serious health complications to the patient caused by the biopsy. For example, patients generally experience extreme pain, and additionally, the liver profusely bleeds after a percutaneous biopsy.

Alternatively, tissue samples may be obtained without the problems associated with a percutaneous biopsy by accessing the liver via a transjugular procedure. Known techniques involve accessing the liver through the jugular vein with an elongated biopsy device. Typically, these biopsy devices are identical to typical single and double action biopsy devices, except that the inner and outer needles are elongated to access the liver from the jugular vein.

A problem associated with this type of biopsy device is that the rigid inner and outer needles are commonly metallic and lack the flexibility to navigate through venous passageways to the targeted tissue site. However, biopsy of an organ deep within the body, such as the liver, requires the biopsy device to be implanted at a significant depth. Since the quality of the specimen is largely dependent on the striking momentum of the biopsy device over this long distance, a degree of stiffness of the needles is necessary to transmit striking force from the firing device to the tip of the coring needles. Thus, what is needed is a needle assembly that provides flexibility without compromising the stiffness and integrity of the needles.

SUMMARY

A flexible biopsy needle assembly includes a flexible coring stylet that is slidably disposed within a flexible outer cannula. The coring stylet includes an elongated body, a tip, a sampling notch in the body adjacent to the tip, and at least one ferrule spaced along the length of the body. The cannula includes an elongated tubular body that defines a lumen sized for sliding passage of the stylet, a cutting edge at the opening of the lumen, and at least one slit along the length of the tubular body. The ferrule has a diameter that permits sliding contact with the lumen of the cannula and that allows the diameter of the ferrule to extend at least partially into the slit. The stylet and cannula are movable relative to each other between a position in which the ferrule is disposed within the slit to significantly limit the flexibility of the cannula, and a position where the ferrule is moved out of the slit to allow the cannula to bend or flex as needed. The cannula may be provided with one or more slit arrays that include slits at different circumferential locations. The ferrule can then be positioned in one of the slits in the array to control the direction of flexibility corresponding to the angular orientation of the slit.

BRIEF DESCRIPTIONS OF DRAWINGS

FIG. 3 is a perspective view of the flexible outer cannula of the flexible biopsy needle assembly shown in FIG. 1.

FIG. 4 is a sectional view of the flexible outer cannula depicting the orientation of a slit in the cannula shown in FIG. 3.

FIG. 5 is a sectional view of the flexible outer cannula depicting the orientation of another slit in the cannula shown in FIG. 3.

FIG. 6 is a sectional view of the flexible outer cannula depicting the orientation of a further slit in the cannula shown in FIG. 3.

DETAILED DESCRIPTION

Figure 1:
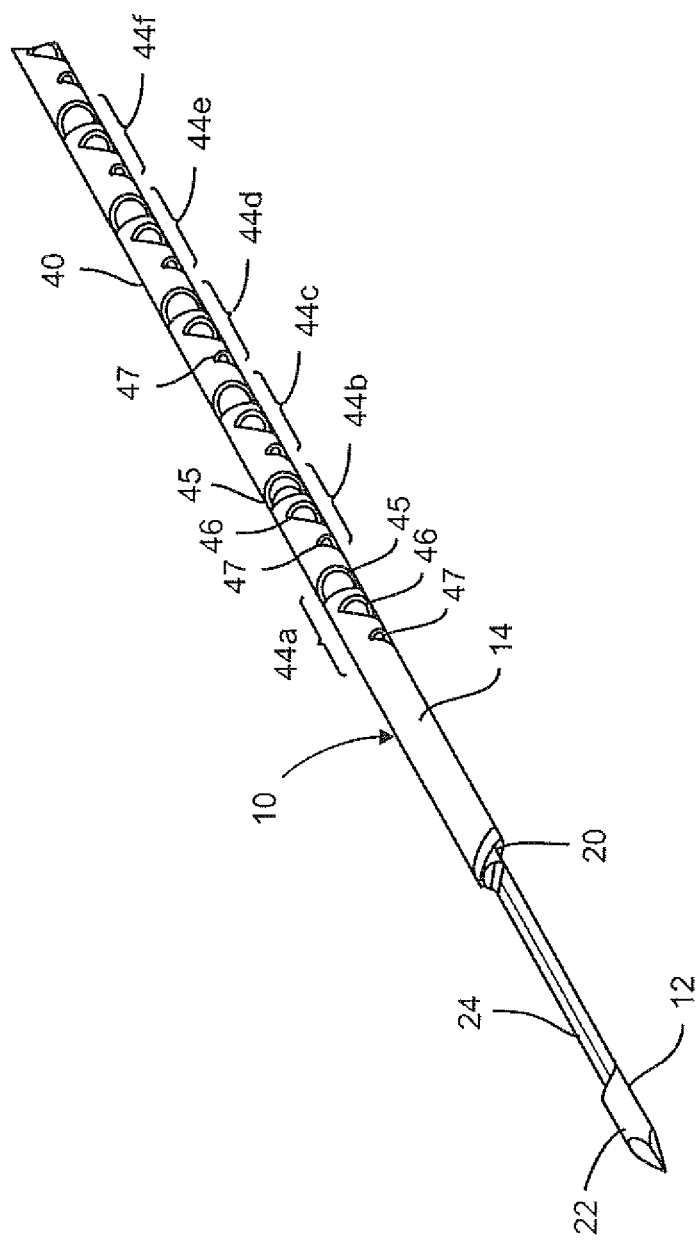
FIG. 1 is a perspective view of the flexible biopsy needle assembly according to the present disclosure.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
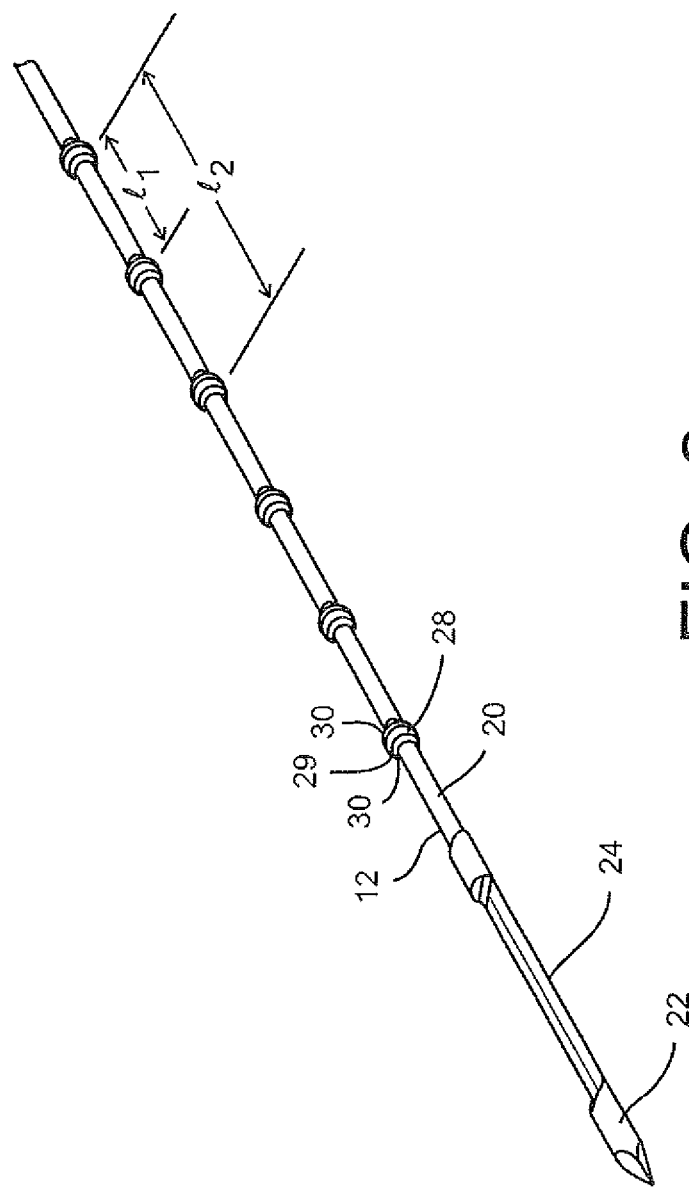
FIG. 2 is a perspective view of the flexible coring stylet of the assembly shown in FIG. 1.

A flexible biopsy needle assembly 10 is provided as shown in FIG. 1. The needle 10 includes a flexible coring stylet 12 that is slidably disposed within a flexible outer cannula 14. As shown in FIG. 2, the coring stylet 12 includes an elongated body 20 that may be in the form of a flexible wire. The tip 22 of the stylet 12 may be configured to penetrate tissue, such as a coring tip of known design. A sampling notch 24 is provided in the body 20 adjacent the tip 22 and is configured in a conventional manner to accept and trap tissue during operation of the biopsy needle assembly 10.

Details of the flexible cannula 14 are shown in FIG. 3. The cannula includes a tubular body 40 that defines a lumen 42 sized for sliding passage of the stylet 12 therethrough. The body 40 may define a cutting edge 43 at the opening of the lumen to sever tissue as the cannula 14 is extended over the sampling notch 24 and tip 22 of the stylet. The stylet and cannula may form part of a biopsy apparatus that permits introduction of the needle assembly into a target tissue, either with the stylet retracted or extended relative to the end of the cannula. When tissue prolapses into the sampling notch 24, either the stylet is retracted or, alternatively, the cannula is extended so that the cutting edge 43 severs the tissue held within the sampling notch. The needle assembly is then withdrawn with the tissue sampling protected within the cannula. The proximal end of the stylet and needle may be configured for engagement within a handpiece configured to permit manipulation and operation of the stylet and needle to perform a biopsy. The handpiece may be of a variety of configurations, such as the handpiece disclosed in U.S. Pat. No. 7,048,694, issued on May 23, 2006, to the assignee of the present invention, the disclosure of which is incorporated herein by reference.

In many instances it is desirable that the needle assembly exhibit a certain amount of flexibility to navigate to the target tissue site. Thus, the body 20 of the stylet 12 is flexible. The outer cannula 14 is likewise made flexible, in part by the imposition of slits in the tubular body 40 of the cannula. The cannula body also may be formed of a material with sufficient flexibility to bend along the length of the cannula and most particularly at the slits formed in the body. The amount of bending is calibrated by the number and location of the slits as well as the width of the slits.

The flexible cannula 14 shown in FIG. 3 includes a series of slit arrays 44 spaced along the length of the tubular body 40. In the illustrated embodiment, each slit array includes three generally V-shaped slits 45, 46 and 47 cut into the tubular body, with the slits spanning about 180° of the circumference of the body. Successive slits are oriented at approximately 45° intervals. Thus, as shown in the cross-sectional views of FIGS. 4-6, the slit 45 is offset about 45° counter-clockwise relative to the vertical, slit 46 is vertically aligned and slit 47 is offset about 45° clockwise from the vertical. As can be seen in FIG. 3, this arrangement of slits in each slit array 44 produces a repeated pattern of slits along the length of the tubular body 40. Slit arrays may extend along the entire length of the cannula, or may be limited to specific locations along the length of the body where greater flexibility is desired.

The elongated or wire body 20 of the stylet 12 is provided with a series of ferrules 28 spaced along the length of the body. The ferrules 28 are spaced so that a ferrule may be aligned with each of the slit arrays 44 in the outer cannula 14. More specifically, the ferrules may be spaced so that all of the ferrules are simultaneously aligned with one of the slits in each array. In one specific embodiment, the ferrules are spaced so that the distance $l_1$ between immediately successive ferrules (FIG. 2) corresponds to the distance between slit 45 in one slit array and middle slit 46 in the immediately successive array. Similarly, the distance $l_2$ between every other ferrule corresponds to the distance between slit 45 in one slit array and last slit 47 in the next successive array. It can be noted that the distance $l_1$ between adjacent successive ferrules 28 is greater than the distance between the slits 45 and 47 in each slit array.

With this arrangement of slits and ferrules, it can be seen in FIG. 1 that a ferrule is positioned within a slit 46 of the first array 44a and within slit 45 of the second array 44b. Since the length $l_1$ is greater than the length of a slit array 44, the next ferrule of the stylet 12 is disposed within the slit 47 of the fourth array 44d, while there is no ferrule in the third slit array 44c.

In one embodiment, each ferrule 28 is provided with a cylindrical central portion 29 that is flanked on each side by a conical portion 30. The central portion 29 has a diameter sized to extend at partially into one of the slits 45, 46, 47. When the central portion 29 of a ferrule 28 is disposed within a slit, such as slit 45, any bending of the tubular body 40 of the cannula is prevented or significantly limited. When the ferrule is moved out of a slit and into the portion of the body 40 between slits, the bending function of the slit is no longer compromised and the cannula is free to bend at the slit as desired. The conical portions 30 facilitate dislodging the cylindrical central portion 29 from a slit. The ferrules can be positioned in particular ones of the slits 45, 46, 47 to control the direction of flexibility corresponding to the angular orientation of the particular slit (as depicted in FIGS. 4-6).

In another feature, the ferrules 28 may be spaced along the length of the body or wire 20 to help stabilize the wire as the stylet 12 is translated within the lumen 42 of the cannula. In particular, the ferrules prevent buckling of the wire 20 as the stylet is extended distally from the cannula and into the target tissue. To accomplish this feature, the central portion 29 of each ferrule may be sized for a close running fit with the lumen 42 of the outer cannula 14.

It should be understood that the components of the biopsy needle assembly 10 disclosed herein are formed of medical grade materials. The tubular body 40 of the outer cannula 14 and the wire body 20 of the stylet are further formed of a material that is sufficiently of flexibility to bend as desired during use, but that is also sufficiently rigid to be advanced into body tissue and a solid tissue mass without compromise. The stylet 20 may be molded from a common material, or may incorporate a material for the tip 22 and notch 24 that is different from the body 20. Similarly, the material of the body 20 may be different from that of the ferrules 28, with the ferrules affixed to the body in a conventional manner, such as by welding, adhering or shrink fit.

It is intended that the specification, drawings and examples be considered as exemplary only, with the true scope and spirit of the invention being indicated by the following claims. It should be understood that only the preferred embodiments have been shown and described and that all changes and modifications that come within the spirit of the invention are desired to be protected.

What is claimed:

1. A selectively bendable biopsy cannula assembly, comprising:
    an elongated flexible inner body sized for introducing into a patient and having at least one ferrule spaced along the length of the body, the ferrule defining a diameter; and
    an elongated flexible tubular body sized for introduction into a patient, and defining a lumen sized for sliding passage of the inner body therethrough, and having at least one slit disposed along the length of the tubular body and said at least one slit defined in and extending between the inner and outer diameter of the tubular body,
    wherein the diameter of the ferrule is sized to extend at least partially into the slit when the ferrule is aligned with said slit and when the elongated flexible tubular body is urged to flex, the bending of the elongated flexible tubular body is prevented or significantly limited.

2. The selectively bendable cannula assembly of claim 1 wherein the tubular body includes a slit array including at least two slits spaced apart along the length of said tubular body.

3. The selectively bendable cannula assembly of claim 2 wherein the at least two slits span 180 degrees of a circumference of the tubular body.

4. The selectively bendable cannula assembly of claim 2 wherein the at least two slits are oriented at 45 degree intervals around a circumference of the tubular body.

5. The selectively bendable cannula assembly of claim 4 wherein the slit array includes three slits, a first one of the slits offset by an angle counter-clockwise from a vertical diameter through the tubular body, an immediately successive second one of the slits aligned along the vertical diameter, and an immediately successive third one of the slits offset clockwise from the vertical diameter.

6. The selectively bendable cannula assembly of claim 5 wherein:
   the tubular body includes at least two of the slit arrays disposed apart along the length of the tubular body; and
   the inner body includes at least two ferrules spaced apart along the length of the inner body so that one each of the ferrules is aligned with one each of the slit arrays.

7. The selectively bendable cannula assembly of claim 6 wherein the at least two ferrules are spaced so that each of the ferrules is simultaneously aligned with one of the slits in each slit array.

8. The selectively bendable cannula assembly of claim 7 wherein the at least two ferrules are spaced so that one of the ferrules is aligned with the first one of the slits in each slit array and a second one of the ferrules is aligned with the second one of the slits in each slit array.

9. The selectively bendable cannula assembly of claim 1 wherein each at least one ferrule includes a cylindrical central portion that is flanked on each side by a conical portion.

10. The selectively bendable cannula assembly of claim 9 wherein the diameter is defined at the central portion.

11. The selectively bendable cannula assembly of claim 2, wherein the inner body and tubular body are movable between a position in which at least one ferrule is disposed within at least one slit to limit bending of the tubular body at the at least one slit, and a position in which the ferrule is moved out of the slit to no longer limit bending of the tubular body at said at least one slit.

12. The selectively bendable cannula assembly of claim 11, wherein the at least two slits are separated around a circumference of the tubular body so bending is limited in different angular orientations depending upon which one of the at least two slits a ferrule is positioned within.

13. The selectively bendable cannula assembly of claim 11 wherein the at least one ferrule includes at least a first ferrule and a second ferrule separated by a distance which is greater than a distance between the at least two slits.

14. The selectively bendable cannula assembly of claim 13 wherein the at least one slit array includes at least a first slit array and a second slit array, wherein each slit array includes three slits, a first one of the slits offset by an angle counter-clockwise from a vertical diameter through the tubular body, an immediately successive second one of the slits aligned along the vertical diameter, and an immediately successive third one of the slits offset clockwise from the vertical diameter by said angle.

15. The selectively bendable cannula assembly of claim 14 wherein the distance between the first ferrule and the second ferrule is greater than the distance between slits having the same orientation in the first slit array and the second slit array.

* * * * *